US008618263B2

(12) United States Patent
Hilden et al.

(10) Patent No.: US 8,618,263 B2
(45) Date of Patent: Dec. 31, 2013

(54) ANTIBODIES AGAINST TISSUE FACTOR PATHWAY INHIBITOR (TFPI)

(75) Inventors: Ida Hilden, Vanløse (DK); Jes Thorn Clausen, Hoeng (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/140,840

(22) PCT Filed: Dec. 18, 2009

(86) PCT No.: PCT/EP2009/067566
§ 371 (c)(1),
(2), (4) Date: Jul. 13, 2011

(87) PCT Pub. No.: WO2010/072687
PCT Pub. Date: Jul. 1, 2010

(65) Prior Publication Data
US 2011/0268745 A1 Nov. 3, 2011

Related U.S. Application Data

(60) Provisional application No. 61/203,512, filed on Dec. 23, 2008.

(30) Foreign Application Priority Data

Dec. 22, 2008 (EP) .................. 081725228

(51) Int. Cl.
*C07K 16/36* (2006.01)
*C07K 16/18* (2006.01)
*A61K 39/395* (2006.01)
*C07K 14/745* (2006.01)

(52) U.S. Cl.
USPC ................. 530/388.25; 424/145.1; 514/14.5

(58) Field of Classification Search
None
See application file for complete search history.

(56) References Cited

FOREIGN PATENT DOCUMENTS

| EP | 539975 | 5/1993 |
|----|--------|--------|
| JP | 8075736 | 3/1996 |

OTHER PUBLICATIONS

Rudikoff et al (1982. Proc Natl Acad Sci USA. 79: 1979-1983).*
MacCallum et al (1996. Journal of Molecular Biology. 262: 732-745).*
Pascalis et al (2002. Journal of Immunology. 169:3076-3084).*
Casset et al (2003. Biochemical and Biophysical Research Communications. 307: 198-205).*
Vajdos et al (2002. Journal of Molecular biology. 320: 415-428).*
Holm et al (2007. Molecular Immunology. 44: 1075-1084).*
Chen et al (1999. Journal of Molecular Biology. 293: 865-881).*
Wu et al (1999. Journal of Molecular Biology. 294: 151-162).*
Abstract of JP 8075736, Dated Mar. 22, 1996.
Yang et al., Medline, Mar. 1, 1997, XP002574353.
R&D Systems, New Products—Jun. 2007, pp. 1-12.
Abiyuma et al., Medline, Jul. 1, 1995, XP002574354.
Erhardtsen et al., Blood Coagulation and Fibrinolysis, 1995, vol. 6, No. 5, pp. 388-394.
Dahm et al., Journal of Thrombosis and Haemostasis, 2005, vol. 3, No. 4, pp. 651-658.
Tang et al., The American Journal of Pathology, 2007, vol. 171, No. 3, pp. 1066-1077.
Winkler et al., Journal of Immunology, 2000, vol. 165, No. 8, pp. 4505-4514.

* cited by examiner

*Primary Examiner* — Zachary Howard
(74) *Attorney, Agent, or Firm* — Michael J. Brignati

(57) ABSTRACT

The invention relates to antibodies that specifically bind to tissue factor pathway inhibitor (TFPI) and that reduce clotting time in (a) human FVIII-deficient plasma and/or (b) human whole blood. Such antibodies have utility in the treatment of bleeding disorders and in the stimulation of blood clotting.

8 Claims, 5 Drawing Sheets

Figure 1
A
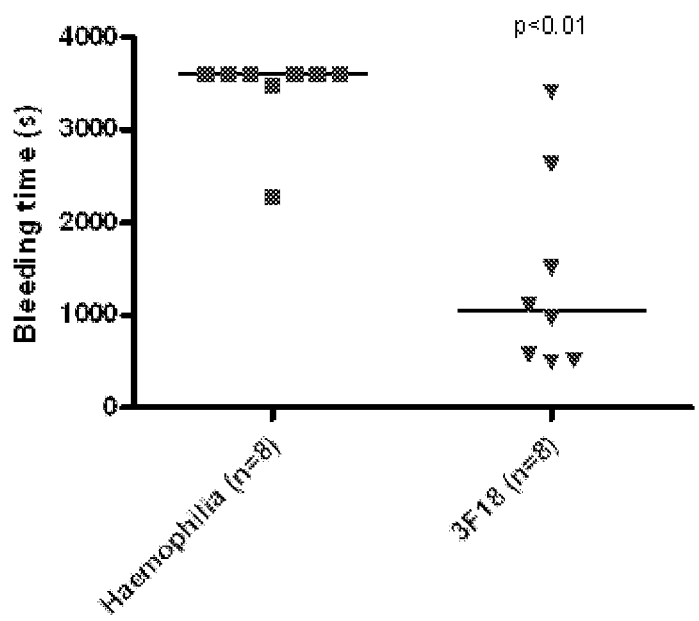
B
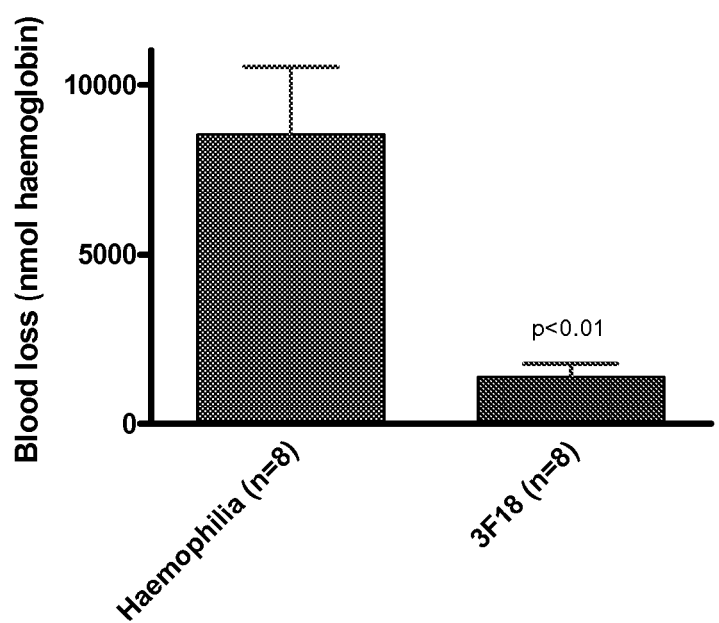

TFPI-3F18A4B1 VL

```
        D   V   V   M       T   Q   T       P   L   T       L   S   V   T       I   G   Q  ·
1       GATGTTGTGA  TGACCCAGAC  TCCACTCACT  TTGTCGGTTA  CCATTGGACA
        CTACAACACT  ACTGGGTCTG  AGGTGAGTGA  AACAGCCAAT  GGTAACCTGT

·P   A   S       I   S   C   K       S   S   Q       S   L   L       D   S   D   G  ·
51      ACCAGCTTCC  ATCTCTTGCA  AGTCAAGTCA  GAGCCTCTTA  GATAGTGATG
        TGGTCGAAGG  TAGAGAACGT  TCAGTTCAGT  CTCGGAGAAT  CTATCACTAC

·K   T   Y       L   N   W       L   L   Q   R       P   G   E       S   P   K
101     GAAAAACCTA  TTTAAATTGG  TTATTACAGA  GGCCAGGCGA  GTCTCCAAAG
        CTTTTTGGAT  AAATTTAACC  AATAATGTCT  CCGGTCCGCT  CAGAGGTTTC

L   L   I   Y       L   V   S       K   L   D       S   G   V       P   D   R   F  ·
151     CTCCTTATCT  ATCTGGTGTC  TAAACTGGAC  TCTGGAGTCC  CTGACAGGTT
        GAGGAATAGA  TAGACCACAG  ATTTGACCTG  AGACCTCAGG  GACTGTCCAA

·T   G   S       G   S   G   T       D   F   T       L   K   I       S   R   V   E  ·
201     CACTGGCAGT  GGATCAGGGA  CAGATTTCAC  ACTGAAAATC  AGCAGAGTGG
        GTGACCGTCA  CCTAGTCCCT  GTCTAAAGTG  TGACTTTTAG  TCGTCTCACC

·A   E   D       L   G   V       Y   Y   C   L       Q   G   T       H   F   P
251     AGGCTGAGGA  TTTGGGAGTT  TATTACTGCT  TACAAGGTAC  ACATTTTCCT
        TCCGACTCCT  AAACCCTCAA  ATAATGACGA  ATGTTCCATG  TGTAAAAGGA

H   T   F   G       G   T       K   L   E       I   K   R
301     CACACGTTCG  GAGGGGGGAC  CAAGCTGGAA  ATAAAACGG
        GTGTGCAAGC  CTCCCCCCTG  GTTCGACCTT  TATTTTGCC
```

B

TFPI-3F18A4B1 VH (nucleotide and translated sequence):

```
        E   V   K   L       V   E   S       G   G   G       L   V   K       P   G   G   S  ·
1       GAAGTGAAGC  TGGTAGAGTC  TGGGGGAGGC  TTGGTGAAGC  CTGGAGGGTC
        CTTCACTTCG  ACCATCTCAG  ACCCCCTCCG  AACCACTTCG  GACCTCCCAG

·L   R   L       S   C   A   A       S   G   F       T   F   S       N   Y   A   L  ·
51      CCTGAGACTC  TCCTGTGCAG  CCTCTGGATT  CACTTTCAGT  AACTATGCCC
        GGACTCTGAG  AGGACACGTC  GGAGACCTAA  GTGAAAGTCA  TTGATACGGG

·S   W   V       R   Q   T       P   D   K   R       L   E   W       V   A   S
101     TGTCTTGGGT  TCGCCAGACT  CCAGACAAGA  GGCTGGAGTG  GGTCGCATCC
        ACAGAACCCA  AGCGGTCTGA  GGTCTGTTCT  CCGACCTCAC  CCAGCGTAGG

I   S   S   G       G   A   T       Y   Y   P       D   S   V       E   G   R   F  ·
151     ATTAGTAGTG  GTGGTGCCAC  CTACTATCCA  GACAGTGTGG  AGGGCCGATT
        TAATCATCAC  CACCACGGTG  GATGATAGGT  CTGTCACACC  TCCCGGCTAA

·T   I   S       R   D   N   V       R   N   I       L   Y   L       Q   M   S   S  ·
201     CACCATCTCC  AGAGATAATG  TCAGGAACAT  CCTGTACCTG  CAAATGAGCA
        GTGGTAGAGG  TCTCTATTAC  AGTCCTTGTA  GGACATGGAC  GTTTACTCGT

·L   Q   S       E   D   T       A   M   Y   Y       C   T   R       G   A   Y
251     GTCTGCAGTC  TGAGGACACG  GCCATGTATT  ACTGTACAAG  AGGAGCCTAC
        CAGACGTCAG  ACTCCTGTGC  CGGTACATAA  TGACATGTTC  TCCTCGGATG

G   S   D   Y       F   D   Y       W   G   Q       G   T   T   L       T   V   S  ·
301     GGCTCGGACT  ACTTTGACTA  CTGGGGCCAA  GGCACCACTC  TCACAGTCTC
        CCGAGCCTGA  TGAAACTGAT  GACCCCGGTT  CCGTGGTGAG  AGTGTCAGAG

·S
351     CTCA
        GAGT
```

```
         1         2          3         4         5         6
1234567890123456789012 34567ABCDEF8901234 5678901234567890 0123456 7890
DVVMTQTPLTLSVTIGQPASISCKSSQSLLDS-DGKTYLNWLLQRPGESPKLLIYLVSKLDSGVPD 7         8         9        10
123456789012345678901234567 89012345AB67 890123456789
RFTGSGSGTDFTLKISRVEAEDLGVYYCLQGTHFP--HTFGGGTKLEIKR
```

B

```
         1         2         3         4         5         6
123456789012345678901234567 89012345AB 67890123456789 012ABC34567890
EVKLVESGGGLVKPGGSLRLSCAASGFTFSNYALS--WVRQTPDKRLEWVASIS---SGGATYYP 7         8         9        10                  11
12345 67890123456789012ABC345678901234 567890ABCDEFGHIJK12 34567890
DSVEGRFTISRDNVRNILYLQMSSLQSEDTAMYYCTRGAYGSDYF---------DYWGQGTTLTVSS
```

Figure 4

```
1          11         21         31         41         51
DSEEDEEHTI ITDTELPPLK LMHSFCAFKA DDGPCKAIMK RFFFNIFTRQ CEEFIYGGCE 61         71         81         91         101        111
GNQNRFESLE ECKKMCTRDN ANRIIKTTLQ QEKPDFCFLE EDPGICRGYI TRYFYNNQTK 121        131        141        151        161        171
QCERFKYGGC LGNMNNFETL EECKNICEDG PNGFQVDNYG TQLNAVNNSL TPQSTKVPSL 181        191        201        211        221        231
FEFHGPSWCL TPADRGLCRA NENRFYYNSV IGKCRPFKYS GCGGNENNFT SKQECLRACK 241        251        261        271
KGFIQRISKG GLIKTKRKRK KQRVKIAYEE IFVKNM
```

ANTIBODIES AGAINST TISSUE FACTOR PATHWAY INHIBITOR (TFPI)

CROSS-REFERENCE TO RELATED APPLICATIONS

This application is a 35 U.S.C. §371 national stage application of International Patent Application PCT/EP2009/067566 (published as WO 2010/072687 A1), filed Dec. 18, 2009, which claimed priority of European Patent Application 08172522.8, filed Dec. 22, 2008; this application further claims priority under 35 U.S.C. §119 of U.S. Provisional Application 61/203,512, filed Dec. 23, 2008.

FIELD OF THE INVENTION

The present invention relates to antibodies that specifically bind to tissue factor pathway inhibitor (TFPI).

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on May 27, 2011. The Sequence Listing is made up of 10,347 bytes, and the information contained in the attached "SEQUENCE LISTING" is identical to the information in the specification as originally filed. No new matter is added.

BACKGROUND TO THE INVENTION

Vessel wall injury exposes tissue factor (TF) to the blood circulation and TF forms a complex with Factor VII/activated Factor VII (FVII/FVIIa) on the surface of TF-bearing cells. This leads to the activation of Factor X (FX) to FXa which together with FVa generates a limited amount of thrombin (FIIa). Small amounts of thrombin activate platelets, and this results in surface exposure of phospholipids that supports the binding of the tenase complex consisting of FVIIIa/FIXa The tenase complex produces large amounts of FXa, which subsequently facilitates a full thrombin burst. A full thrombin burst is needed for the formation of a mechanically strong fibrin structure and stabilization of the haemostatic plug. FVIII or FIX is missing or present at low levels in haemophilia patients, and due to the lack of tenase activity, the capacity to generate FXa is low and insufficient to support the propagation phase of the coagulation. In contrast, the TF-mediated initiation phase is not dependent on the formation of the tenase complex. However, the TF-pathway will, shortly after an initial FXa generation, be blocked by plasma inhibitors.

Tissue factor pathway inhibitor (TFPI) downregulates ongoing coagulation by neutralizing the catalytic activity of FXa and by inhibition of the TF-FVIIa complex in the presence of FXa. TFPI either inhibits the TF/FVIIa/FXa complex on the cellular surface or inhibits released FXa followed by FVIIa/TF inhibition.

SUMMARY OF THE INVENTION

The Inventors have identified antibodies which specifically bind to TFPI and thereby modulate its activity. The present invention relates to these antibodies and to other related antibodies that are derived from these antibodies or have similar binding properties to these antibodies.

Accordingly, the present invention relates to antibodies that specifically bind to tissue factor pathway inhibitor (TFPI) and that reduce clotting time in (a) human FVIII-deficient plasma and/or (b) human whole blood.

Preferred antibodies comprise the light chain variable region of SEQ ID NO: 3 and the heavy chain variable region of SEQ ID NO: 6.

The invention also provides polynucleotides which encode an antibody of the invention, such as polynucleotides which encode an antibody light chain and/or an antibody heavy chain of the invention.

The invention also provides pharmaceutical compositions comprising an antibody or polynucleotide of the invention and a pharmaceutically acceptable carrier or diluent.

The antibodies, polynucleotides and compositions of the invention are also provided for use in (a) the treatment or prevention of a bleeding disorder or (b) the stimulation of blood clotting. That is, the invention provides a method for (a) the treatment or prevention of a bleeding disorder or (b) the stimulation of blood clotting, the method comprising administering to a patient in need thereof a therapeutically or prophylactically effective amount of an antibody, polynucleotide or composition of the invention.

BRIEF DESCRIPTION OF THE FIGURES

FIGS. 1A and 1B show the cuticle bleeding time measured in transient haemophiliac rabbits following treatment with control IgG (Haemophilia) or the anti-TFPI antibody TFPI-3F18A2 (3F18).

FIG. 2 shows the nucleotide sequences and translated polypeptide sequences for the VH (SEQ ID NO: 5) and VL (SEQ ID NO: 2) sequences of the antibody TFPI-3F18A4B1.

FIG. 3 shows the amino acid sequences of the VL (A) (SEQ ID NO: 3) and VH (B) (SEQ ID NO: 6) of the 3F18 antibody. Numbering above the sequences is shown according to Kabat. Positions corresponding to CDR loops are highlighted in bold underlined text in the Kabat numbering.

FIG. 4 shows the sequence of TFPI1 (SEQ ID NO: 1). The Kunitz domains are shown in bold: TFPI1 Kunitz domain 1=amino acids 26 to 76; TFPI1 Kunitz domain 2=amino acids 97-147; TFPI1 Kunitz domain 3=amino acids 188-238. The C-terminal part of TFPI1 is shown in italics at amino acids 240 to 276.

BRIEF DESCRIPTION OF THE SEQUENCE LISTING

Figure 5:
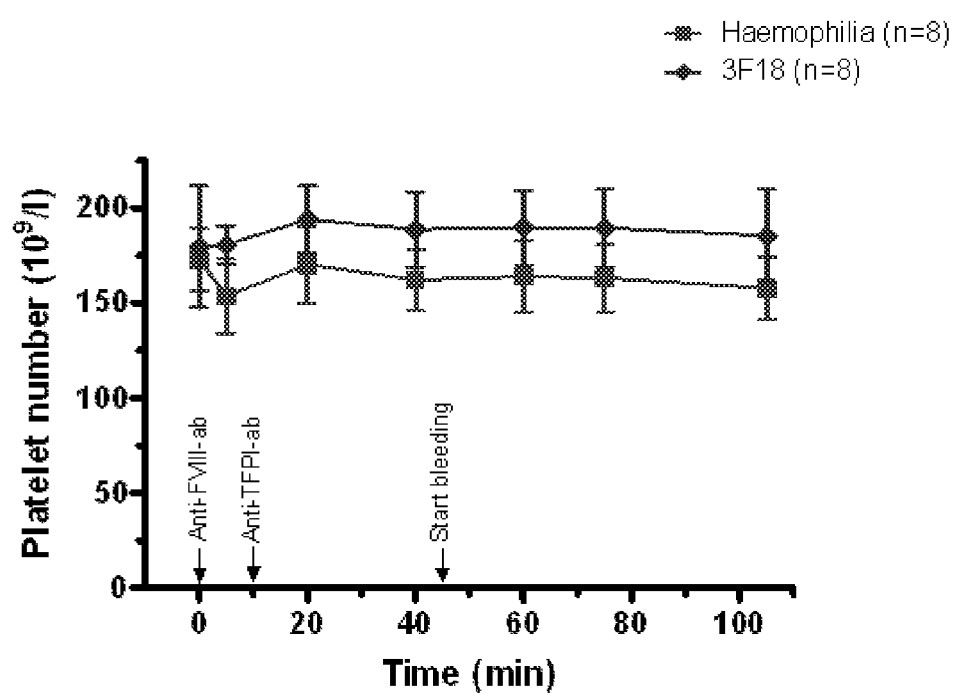
FIG. 5 shows the platelet number following stimulation with anti-FVIII antibody, anti-TFPI-antibody and then bleed. This was carried out in a control haemophilia model and in the presence of the anti-TFPI antibody 3F18 as described herein.

SEQ ID NO: 1 gives the amino acid sequence of human TFPI1.

SEQ ID Nos 2 to 4 give the polynucleotide (coding and complement) and polypeptide sequences for the light chain variable domain (VL) of the TFPI-3F18A4B1 monoclonal antibody.

SEQ ID Nos 5 to 7 give the polynucleotide (coding and complement) and polypeptide sequences for the heavy chain variable domain (VH) of the TFPI-3F18A4B1 monoclonal antibody.

SEQ ID NO: 8 gives the sequence of a reverse primer used for heavy chain variable domain amplification and SEQ ID NO: 9 gives the sequence of a reverse primer used for light chain amplification.

DETAILED DESCRIPTION OF THE INVENTION

The present invention relates to antibodies that bind to TFPI. The antibodies preferably specifically bind to TFPI, i.e. they bind to TFPI but they do not bind, or bind at a lower affinity, to other molecules. In particular, the invention relates to antibodies that bind to TFPI and that modulate its activity. Antibodies of the invention may thus possess the ability to shorten clotting time. For example, an antibody of the invention may have the ability to shorten clotting time in human FVIII-deficient plasma or to reduce time to clot by thromboelastography (TEG) analysis of human whole blood. The invention also relates to uses for such antibodies, such as therapeutic and pharmaceutical uses.

The term TFPI as used herein encompasses any naturally occurring form of TFPI which may be derived from any suitable organism. For example, TFPI for use as described herein may be a mammalian TFPI, such as human, mouse, rat, primate, bovine, ovine, or porcine TFPI. Preferably the TFPI is human TFPI. The TFPI may be a mature form of TFPI such as a TFPI protein that has undergone post-translational processing within a suitable cell. Such a mature TFPI protein may, for example, be glycosylated. The TFPI may be a full length TFPI protein. The term TFPI also encompasses variants, isoforms and other homologs of such TFPI molecules. Variant TFPI molecules will generally be characterised by having the same type of activity as naturally occurring TFPI, such as the ability to convert neutralize the catalytic activity of FXa, or the ability to inhibit a complex of TF-FVIIa/FXa.

An antibody of the invention will have the ability to bind to TFPI. Preferably, an antibody of the invention will bind specifically to TFPI. That is, an antibody of the invention will preferably bind to TFPI with greater binding affinity than that at which it binds to another molecule. An antibody of the invention may have the ability to bind or specifically bind to a TFPI molecule as described herein such as any target molecule as described herein.

The terms "binding activity" and "binding affinity" are intended to refer to the tendency of an antibody molecule to bind or not to bind to a target. Binding affinity may be quantified by determining the dissociation constant (Kd) for an antibody and its target. Similarly, the specificity of binding of an antibody to its target may be defined in terms of the comparative dissociation constants (Kd) of the antibody for its target as compared to the dissociation constant with respect to the antibody and another, non-target molecule.

Typically, the Kd for the antibody with respect to the target will be 2-fold, preferably 5-fold, more preferably 10-fold less than Kd with respect to the other, non-target molecule such as unrelated material or accompanying material in the environment. More preferably, the Kd will be 50-fold less, even more preferably 100-fold less, and yet more preferably 200-fold less.

The value of this dissociation constant can be determined directly by well-known methods, and can be computed even for complex mixtures by methods such as those, for example, set forth in Caceci et al. (Byte 9:340-362, 1984). For example, the Kd may be established using a double-filter nitrocellulose filter binding assay such as that disclosed by Wong & Lohman (Proc. Natl. Acad. Sci. USA 90, 5428-5432, 1993). Other standard assays to evaluate the binding ability of ligands such as antibodies towards targets are known in the art, including for example, ELISAs, Western blots, RIAs, and flow cytometry analysis. The binding kinetics (e.g., binding affinity) of the antibody also can be assessed by standard assays known in the art, such as by Biacore™ system analysis.

A competitive binding assay can be conducted in which the binding of the antibody to the target is compared to the binding of the target by another, known ligand of that target, such as another antibody. The concentration at which 50% inhibition occurs is known as the Ki. Under ideal conditions, the Ki is equivalent to Kd. The Ki value will never be less than the Kd, so measurement of Ki can conveniently be substituted to provide an upper limit for Kd.

Preferred Kd (or Ki) values for an antibody of the invention may be at least $1\times10^{-11}$M, at least $1\times10^{-10}$M, at least $1\times10^{-9}$M pr $1\times10^{-8}$M. An antibody of the invention may have a Kd (or Ki) for its target of $1\times10^{-7}$M or less, $1\times10^{-8}$M or less or $1\times10^{-9}$M or less.

An antibody that specifically binds its target may bind its target with a high affinity, such as a Kd (or Ki) as discussed above, and may bind to other, non-target molecules with a lower affinity. For example, the antibody may bind to a non-target molecules with a Kd (or Ki) of $1\times10^{-6}$M or more, more preferably $1\times10^{-5}$ M or more, more preferably $1\times10^{-4}$ M or more, more preferably $1\times10^{-3}$ M or more, even more preferably $1\times10^{-2}$ M or more. An antibody of the invention is preferably capable of binding to its target with an affinity that is at least two-fold, 10-fold, 50-fold, 100-fold or greater than its affinity for binding to an other non-target molecule.

The target molecule may be any TFPI molecule as described herein, such as a naturally occurring TFPI molecule, a fully mature TFPI molecule or a full-length TFPI molecule. Preferred TFPI molecules are fully mature, naturally occurring, full length mammalian TFPI molecules. For example, the TFPI molecule may consist of, or may comprise, the amino acid sequence of SEQ ID NO: 1 or a fragment or other variant thereof as described herein.

The target molecule may be a variant of a TFPI molecule such as a fragment of a TFPI molecule. For example, the target molecule may be a fragment or other variant of TFPI which maintains a suitable epitope for antibody binding. For example, the target molecule may be a fragment or other variant of TFPI which retains an epitope as described herein. The target molecule may comprise such an epitope.

In one embodiment, the target molecule is a full length TFPI molecule. The full length TFPI molecule may comprise a first, second and third Kunitz domain as described herein. The full length TFPI molecule may comprise a first, second and third Kunitz domain as described herein and also a carboxy terminal region as described herein. The full length TFPI molecule may be a naturally occurring TFPI molecule such as a full length TFPI polypeptide as expressed from a TFPI gene, or as secreted by TFPI expressing cells. The full length TFPI molecule may be a naturally occurring TFPI molecule as found circulating in free form in plasma. The full length TFPI molecule is not a truncated TFPI molecule such as a naturally-occurring truncated TFPI molecule as described herein.

In one embodiment, the target molecule is a truncated TFPI molecule. For example, the truncated TFPI molecule may comprise a carboxy terminal truncation. For example, a number of naturally-occurring truncated forms of TFPI are known. These may comprise a truncation of part or all of the carboxy terminal part of TFPI. They may further comprise truncation of part or all of one or more of the Kunitz domains. For example, a truncated form of TFPI may comprise the deletion of the carboxy terminal part and part or all of the third Kunitz domain.

Truncated TFPI is preferably used as a target molecule when antibodies are desired to be directed against specific truncated forms of TFPI such as naturally occurring truncated TFPI. For example, one naturally occurring truncated form of TFPI comprises only amino acids 1 to 161 of the full length TFPI molecule (referred to herein as TFPI (1-161)). TFPI (1-161) is an active form of TFPI that has reduced activity compared with the full length molecule. TFPI (1-161) differs in structure from full length TFPI and antibodies generated against TFPI (1-161) as a target molecule may therefore differ from antibodies generated against full length TFPI In one embodiment the target molecule is a naturally-occurring form of TFPI. This may be used in a form in which it is present in vivo. For example, the target molecule may be a full length naturally-occurring TFPI as discussed above. The target molecule may be a truncated naturally-occurring TFPI as discussed above. The target molecule may be TFPI in a form in which it is present in plasma in vivo. The target molecule may be TFPI that is bound to lipoprotein in the same way as is present in plasma in vivo. The target molecule may be TFPI that is bound to cells in the same way as occurs in vivo, such as TFPI that is bound to endothelial cells. An antibody of the invention may bind to any one or more of these naturally occurring forms of TFPI. The antibody of the invention may be able to bind to all of these naturally occurring forms of TFPI, or may be able to discriminate between these different forms, binding to some but not others.

The target molecule may be or may comprise a Kunitz domain of TFPI. Such a target molecule may comprise amino acids 26-76 of SEQ ID NO: 1 or an equivalent Kunitz domain 1 region from another TFPI polypeptide. Such a target molecule may comprise amino acids 97 to 147 of SEQ ID NO: 1 or amino acids 91 to 150 of SEQ ID NO: 1 or an equivalent Kunitz domain 2 region from another TFPI polypeptide. Such a target molecule may comprise amino acids 188 to 138 of SEQ ID NO: 1 or an equivalent Kunitz domain 3 region from another TFPI polypeptide. The target molecule may be, or may comprise, a fragment of a Kunitz domain of TFPI. For example, the target molecule may comprise five or more, eight or more, ten or more, twelve or more or fifteen or more amino acids from a Kunitz domain.

The target molecule may be or may comprise the carboxy terminal part of TFPI. The carboxy terminal part of TFPI may be defined as that part of the amino acid sequence of TFPI which lies between the third Kunitz domain and the C terminal of the protein. Such a target molecule may comprise amino acids 240-276 of SEQ ID NO: 1 or an equivalent carboxy terminal region from another TFPI polypeptide. The target molecule may be, or may comprise, a fragment of the carboxy terminal part of TFPI. For example, the target molecule may comprise five or more, eight or more, ten or more, twelve or more or fifteen or more amino acids from the carboxy terminal part of TFPI.

The target molecule may comprise five or more, eight or more, ten or more, twelve or more or fifteen or more surface accessible residues of TFPI or of a particular region of TFPI such as a particular Kunitz domain or the C terminal part of TFPI. A surface accessible residue is a residue having more than 40% relative accessibility For example, for the Kunitz 2 domain of TFPI1 (see SEQ ID NO: 1), the following amino acids have a greater than 40% relative accessibility: 94-95, 98, 100-110, 118-121, 123-124, 131, 134, 138-142 and 144-145. The target molecule may comprise five or more, eight or more, ten or more, twelve or more or fifteen or more of these residues, such as a fragment of TFPI that includes five or more, eight or more, ten or more, twelve or more or fifteen or more of these residues. For the Kunitz 1 domain of TFPI1 (see SEQ ID NO: 1), the following amino acids are expected to have a greater than 40% relative accessibility: 23-24, 27, 28-41, 47-50, 52-53, 60-65, 67-71 and 73-74. The target molecule may comprise five or more, eight or more, ten or more, twelve or more or fifteen or more of these residues, such as a fragment of TFPI that includes five or more, eight or more, ten or more, twelve or more or fifteen or more of these residues. For the Kunitz 3 domain of TFPI1 (see SEQ ID NO: 1), the following amino acids are expected to have a greater than 40% relative accessibility: 186-187, 190, 192-208, 213, 215-220, 225-228, 230-234 and 236-237. The target molecule may comprise five or more, eight or more, ten or more, twelve or more or fifteen or more of these residues, such as a fragment of TFPI that includes five or more, eight or more, ten or more, twelve or more or fifteen or more of these residues.

The target molecule may comprise a known epitope from TFPI. The antibody may thus bind to the same epitope as another known antibody of the invention.

As used herein, the term "epitope" generally refers to the site on a target antigen which is recognised by an immune receptor such as an antibody. Preferably it is a short peptide derived from or as part of a protein. However the term is also intended to include peptides with glycopeptides and carbohydrate epitopes. A single antigenic molecule, such as a target protein as described herein, may comprise several different epitopes. Epitopes can be identified from knowledge of the amino acid and corresponding DNA sequences of the peptide, as well as from the nature of particular amino acids (e.g., size, charge, etc.) and the codon dictionary, without undue experimentation. See, e.g., Ivan Roitt, Essential Immunology, 1988; Janis Kuby, Immunology, 1992 e.g., pp. 79-81.

The location of an epitope may be identified by routine methods. For example, the general location of an epitope may be determined by assessing the ability of an antibody to bind to different fragments or variant TFPI polypeptides. The specific amino acids within TFPI that make contact with an antibody may also be determined using routine methods, such as that described in the Examples. For example, the antibody and target molecule may be combined and the antibody/target complex may be crystallised. The crystal structure of the complex may be determined and used to identify specific sites of interaction between the antibody and its target.

An antibody of the invention may bind to the same epitope or region as another antibody of the invention. For example, where an antibody of the invention is known, other antibodies of the invention may be identified by comparing their binding to TFPI with that of the known antibody. An antibody of the invention may bind to the same epitope or region as the 3F18 antibody described herein.

An antibody of the invention may have the ability to cross-compete with another antibody of the invention for binding to TFPI or another appropriate target as described herein. For example, an antibody of the invention may cross-compete with the 3F18 antibody described herein for binding to TFPI or to a suitable fragment or variant of TFPI that is bound by the 3F18 antibody, such as a target molecule as described herein. Such cross-competing antibodies can be identified based on their ability to cross-compete with a known antibody of the invention in standard binding assays. For example, BIAcore analysis, ELISA assays or flow cytometry may be used to demonstrate cross-competition. Such cross-competition may suggest that the two antibodies bind to the same or similar epitopes.

An antibody of the invention may therefore be identified by a method that comprises such a binding assay which assesses whether or not a test antibody is able to cross-compete with a known antibody of the invention for a binding site on the target molecule. Methods for carrying out competitive binding assays are well known in the art. For example they may involve contacting together a known antibody of the invention and a target molecule under conditions under which the antibody can bind to the target molecule. The antibody/target complex may then be contacted with a test antibody and the extent to which the test antibody is able to displace the antibody of the invention from antibody/target complexes may be assessed. An alternative method may involve contacting a test antibody with a target molecule under conditions that allow for antibody binding, then adding an antibody of the invention that is capable of binding that target molecule and assessing the extent to which the antibody of the invention is able to displace the test antibody from antibody/target complexes.

The ability of a test antibody to inhibit the binding of an antibody of the invention to the target demonstrates that the test compound can compete with an antibody of the invention for binding to the target and thus that the test antibody binds to the same epitope or region on the TFPI protein as the known antibody of the invention. A test antibody that is identified as cross-competing with a known antibody of the invention in such a method is also a potential antibody according to the present invention. The fact that the test antibody can bind TFPI in the same region as a known antibody of the invention and cross-compete with the known antibody of the invention suggests that the test antibody may act as a ligand at the same binding site as the known antibody and that the test antibody may therefore mimic the action of the known antibody. This can be confirmed by assessing the activity of TFPI in the presence of the test compound as described herein.

The known antibody of the invention may be an antibody as described herein, such as the TFPI-3F18A4B1 (3F18) antibody as described herein or any variant or fragment thereof as described herein that retains the ability to bind to TFPI.

An antibody of the invention may bind to the same epitope as the 3F18 antibody, the as described herein or any variant or fragment thereof as described herein that retains the ability to bind to TFPI.

Specific binding may be assessed with reference to binding of the antibody to a molecule that is not the target. This comparison may be made by comparing the ability of an antibody to bind to the target and to another molecule. This comparison may be made as described above in an assessment of Kd or Ki. The other molecule used in such a comparison may be any molecule that is not the target molecule. Preferably the other molecule is not identical to the target molecule. Preferably the target molecule is not a fragment of the target molecule.

An antibody of the invention may bind to its target but not bind to a peptide or protein that (a) does not have an identical amino acid sequence to the target and (b) is not a fragment of the target. For example, where the target is TFPI or a specific fragment or epitope thereof, an antibody of the invention may bind to the TFPI, fragment or epitope, but does not bind to a peptide or protein that (a) has an identical sequence to the TFPI, fragment or epitope and (b) is not a fragment of said TFPI, fragment or epitope.

The other molecule used to determine specific binding may be unrelated in structure or function to the target. For example, the other molecule may be an unrelated material or accompanying material in the environment.

The other molecule used to determine specific binding may be another molecule involved in the same in vivo pathway as the target molecule. For example, where the target is TFPI or a fragment or variant thereof, the other molecule used for comparison may be a protein that forms part of the blood coagulation cascade. By ensuring that the antibody of the invention has specificity for TFPI over another such molecule, unwanted in vivo cross-reactivity may be avoided.

The other molecule used for comparison may be related to the target molecule. For example, where it is desired to identify an antibody that binds only to a specific epitope, the other molecule for comparison may be a TFPI molecule in which that epitope is lacking or disrupted. The other molecule used for comparison may thus be another target molecule that is different to the target molecule bound by the antibody in question.

The antibody of the invention may retain the ability to bind to some molecules that are related to the target molecule. For example, a full-length mature human TFPI may be used as the target, but the antibody may also be able to bind to, e.g. immature forms of human TFPI, fragments or truncated forms of human TFPI, TFPI that is bound to lipoprotein or to a cell or TFPI from other species, such as other mammalian TFPI.

Alternatively, the antibody of the invention may have specificity for a particular target molecule. For example, it may bind to one target molecule as described herein, but may not bind, or may bind with significantly reduced affinity to a different target molecule as described herein. For example, a full length mature human TFPI may be used as the target, but the antibody that binds to that target may be unable to bind to or may bind with lesser affinity to, e.g. immature forms of human TFPI, fragments or truncated forms of human TFPI, TFPI that is bound to lipoprotein or to a cell or TFPI from other species, such as other mammalian TFPI.

An antibody of the invention may bind to TFPI and in doing so may inhibit an activity of TFPI.

As explained above, TFPI downregulates blood coagulation. It does this by inhibiting the activity of FXa and by inhibiting the TF-FVIIa complex in the presence of FXa. The activity of TFPI that is inhibited by an antibody of the invention may be any of these activities or any downstream effect thereof. For example, an antibody of the invention may lead to an increase in blood coagulation, an increase in the presence or levels of FXa or an increased activity of TF-FVIIa. Preferably, an antibody of the invention reduces clotting time when contacted with (a) human FVIII deficient plasma or (b) human whole blood.

The measurement of TFPI activity may comprise assessing the activity of the TFPI in inhibiting coagulation or reducing clotting time in a blood sample. For example, such a method may comprise contacting TFPI with a sample of blood or a blood product such as plasma or serum that comprises blood coagulation factors under conditions in which coagulation should occur, and determining whether coagulation of the blood is inhibited or clotting time is reduced by the presence of the TFPI. The level of blood coagulation or clotting time in such a sample may then be compared to that in an equivalent sample in which a test antibody is also present. If the level of coagulation is increased or clotting time is reduced in the antibody sample, this suggests that the antibody is inhibiting the activity of TFPI in the sample.

Blood coagulation may be detected by looking for coagulation of the blood itself, or one or more characteristics of the coagulation cascade that lie downstream to the point of action of TFPI. For example, the method may assess levels of FXa or activation of TF-FVIIa in the sample.

Various other methods for assessing blood coagulation and clotting time are well known in the art. For example, any effect of an antibody on blood clotting time may be assessed using a dilute prothrombin time analysis as described in the Examples. Briefly, human plasma is contacted with human thromboplastin. The time taken for the plasma to clot is measured in the presence and absence of the test antibody. A positive control may be used in such an analysis, such as addition of FVIIa which would be expected to reduce clotting time. An antibody of the invention should be capable of reducing clotting time in such a method. Preferably, an antibody of the invention should be capable of reducing clotting time in a dose-dependent manner.

Thromboelastography may be used to assess the kinetics of clot formation and fibrinolysis in samples of whole blood. The ability of an antibody to reduce clotting time or to stimulate blood coagulation may thus be similarly assessed in a whole blood sample by comparing the time taken for clot formation in the presence and absence of the antibody.

Methods to assess the functional effects of an antibody of the invention may thus be carried out in vitro. Such methods are preferably carried out on samples of human blood or plasma. Such samples may be normal human blood or plasma or may be deficient in, or supplemented with, one or more factors involved in blood coagulation. For example, these methods may be carried out using normal human whole blood, normal human plasma or FVIII-deficient plasma or whole blood. FVIII-deficient blood or plasma may be generated by contacting a suitable blood or plasma sample with neutralising anti-FVIII antibody.

Preferably, an antibody of the invention is capable of reducing clotting time and/or stimulating blood coagulation in a sample of (a) human whole blood, (b) human plasma, (c) FVIII-deficient human whole blood or (d) FVIII-deficient human plasma.

Methods to determine the ability of an antibody to stimulate blood coagulation or reduce clotting time may also be carried out in vivo. For example, in vivo studies may be carried out in transient haemophilic rabbits as described in the Examples. Briefly, rabbits may be made transient haemophilic by administration of anti-FVIII antibody. The test antibody may then be administered and cuticle bleed time and/or platelet number assessed. A reduction in cuticle bleed time in the presence of a test antibody indicates that the antibody is capable of reducing clotting time and stimulating blood coagulation. An antibody having such an effect may therefore be an antibody of the present invention.

An antibody of the present invention may also lead to no significant decrease in platelet numbers. In particular, an antibody of the invention may be capable of reducing clotting time and/or stimulating blood coagulation in a sample of (a) human whole blood, (b) human plasma, (c) FVIII-deficient human whole blood or (d) FVIII-deficient human plasma or in an animal in vivo without leading to any significant decrease in platelet numbers. Platelet numbers can be assessed in the same sample or animal as the other effects discussed above, or can be assessed separately. For example, platelet numbers can be assessed in a blood sample such as a sample of blood obtained from a patient or experimental animal. Platelet numbers may be assessed following administration of the antibody to a transient haemophilic rabbit as described above. Preferred antibodies of the invention are capable of reducing cuticle bleed time in a transient haemophilic rabbit without leading to a concurrent decrease in platelet numbers. A change in platelet numbers may be assessed by comparing platelet numbers before and after administration of the antibody or by comparing platelet numbers between a sample or animal treated with the antibody of interest and a control sample or animal not treated with that antibody. Preferably, there will be no difference or no statistically significant difference in platelet numbers when making such comparisons. That is, the antibody of the invention will not have caused any decrease in platelet numbers.

The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

An antibody of the invention may be a monoclonal antibody or a polyclonal antibody. In one embodiment, an antibody of the invention is a monoclonal antibody. An antibody of the invention may be a chimeric antibody, a CDR-grafted antibody, a human or humanised antibody or an antigen binding portion of any thereof. For the production of both monoclonal and polyclonal antibodies, the experimental animal is suitably a mammal such as a goat, rabbit, rat or mouse.

Polyclonal antibodies are antibodies that are derived from different B cell lines. A polyclonal antibody may comprise a mixture of different immunoglobulin molecules that are directed against a specific antigen. The polyclonal antibody may comprise a mixture of different immunoglobulin molecules that bind to one or more different epitopes within an antigen molecule. Polyclonal antibodies may be produced by routine methods such as immunisation of a suitable animal, with the antigen of interest. Blood may be subsequently removed from the animal and the IgI fraction purified.

Monoclonal antibodies are immunoglobulin molecules that are identical to each other and have a single binding specificity and affinity for a particular epitope. Monoclonal antibodies (mAbs) of the present invention can be produced by a variety of techniques, including conventional monoclonal antibody methodology e.g., the standard somatic cell hybridization technique of Kohler and Milstein (1975) Nature 256: 495, or viral or oncogenic transformation of B lymphocytes. The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

To generate hybridomas producing monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. The antibody secreting hybridomas can be replated, screened again, and if still positive for suitable IgG, the monoclonal antibodies can be subcloned at least twice by limiting dilution. The stable subclones can then be cultured in vitro to generate small amounts of antibody in tissue culture medium for characterization.

The term "antigen-binding portion" of an antibody refers to one or more fragments of an antibody that retain the ability to specifically bind to an antigen, such as TFPI or another target protein as described herein. It has been shown that the antigen-binding function of an antibody can be performed by fragments of a full-length antibody. Examples of binding fragments encompassed within the term "antigen-binding portion" of an antibody include a Fab fragment, a F(ab')₂ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. These antibody fragments may be obtained using conventional techniques known to those of skill in the art, and the fragments may be screened for utility in the same manner as intact antibodies.

An antibody of the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

An antibody of the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

Antibodies of the invention can be tested for binding to the target protein by, for example, standard ELISA or Western blotting. An ELISA assay can also be used to screen for hybridomas that show positive reactivity with the target protein. The binding specificity of an antibody may also be determined by monitoring binding of the antibody to cells expressing the target protein, for example by flow cytometry.

The specificity of an antibody of the invention for target protein may be further studied by determining whether or not the antibody binds to other proteins. For example, where it is desired to produce an antibody that specifically binds TFPI or a particular part, e.g. epitope, of TFPI, the specificity of the antibody may be assessed by determining whether or not the antibody also binds to other molecules or modified forms of TFPI that lack the part of interest.

As explained above, antibodies of the invention may modify the activity of TFPI. Antibodies having the required binding properties may thus be further tested to determine their effects on the activity of TFPI. Thus, methods may be used to identify suitable antibodies that are capable of binding to TFPI and that are capable of modifying, and in particular reducing, its activity.

Once a suitable antibody has been identified and selected, the amino acid sequence of the antibody may be identified by methods known in the art. The genes encoding the antibody can be cloned using degenerate primers. The antibody may be recombinantly produced by routine methods.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including glycine and both the D or L optical isomers, and amino acid analogs and peptidomimetics.

The present inventors have identified an antibody as described in the examples. This antibody is referred to herein as TFPI-3F18A4B1 or 3F18. The present invention encompasses this antibody and variants and fragments thereof which retain one or more activities of this antibody. The activities of these antibody include the ability to bind to TFPI, the ability to bind to specific locations in the TFPI molecule and the ability to inhibit the activity of TFPI, optionally without leading to a drop in platelet numbers.

A suitable fragment or variant of any of these antibodies will retain the ability to bind to TFPI. It will preferably retain the ability to specifically bind to TFPI. It will preferably retain the ability to specifically bind to the same epitope or region of the TFPI molecule as the antibody (3F18) from which it is derived. It will preferably retain one or more additional functions of the antibody from which it is derived, such as the ability to inhibit TFPI activity or the ability to reduce clotting time, optionally without leading to a drop in platelet numbers.

Polypeptide or antibody "fragments" according to the invention may be made by truncation, e.g. by removal of one or more amino acids from the N and/or C-terminal ends of a polypeptide. Up to 10, up to 20, up to 30, up to 40 or more amino acids may be removed from the N and/or C terminal in this way. Fragments may also be generated by one or more internal deletions.

An antibody of the invention may be, or may comprise, a fragment of the 3F18 antibody or a variant thereof. The antibody of the invention may be or may comprise an antigen binding portion of this antibody or a variant thereof as discussed further above. For example, the antibody of the invention may be an Fab fragment of this antibody or a variant thereof or may be a single chain antibody derived from this antibody or a variant thereof.

The amino acid sequences for the VL and VH chains of the 3F18 antibody are given in SEQ ID Nos: 3 and 6 respectively.

An antibody of the invention may comprise the 3F18 VL amino acid sequence shown in SEQ ID NO: 3 or a fragment or variant thereof. An antibody may additionally or alternatively comprise the 3F18 VL amino acid sequence shown in SEQ ID NO: 6 or a fragment or variant thereof as described herein.

An antibody of the invention may comprise a fragment of one of the VL or VH amino acid sequences shown in FIG. 2.

For example, an antibody of the invention may comprise a fragment of at least 7, at least 8, at least 9, at least 10, at least 12, at least 15, at least 18, at least 20 or at least 25 consecutive amino acids from SEQ ID Nos 3 or 6. Such a fragment will preferably retain one or more of the functions discussed above, such as the ability to bind to TFPI.

A suitable fragment or variant of any of these VH or VL sequences will retain the ability to bind to TFPI. It will preferably retain the ability to specifically bind to TFPI. It will preferably retain the ability to specifically bind to the same epitope or region of the TFPI molecule as the antibody (3F18) from which it is derived. It will preferably retain one or more additional functions of the antibody from which it is derived, such as the ability to inhibit TFPI activity or the ability to reduce clotting time.

An antibody of the invention may comprise a CDR region from one of the three specific antibodies identified herein such as a CDR region from within SEQ ID NO: 3 or 6. Methods for identifying CDR regions are known in the art. The location of CDRs may be assessed in silico, for example by assigning numbering according to Kabat. The locations of amino acid residues involved in antibody binding, either in the antibody molecule or in the epitope, may be assessed experimentally by X ray crystallisation of the complex formed between an antibody and its epitope. Distances between the two molecules may be assessed. For example, the paratope in the antibody and the epitope in the antigen may be identified as comprising those amino acids having a heavy atom within a distance of 4 A from a heavy atom in the other molecule.

For example, as shown in FIG. 3, using Kabat numbering, the CDR sequences within the light chain of 3F18 may be identified at amino acids 24 to 39, 55 to 61 and 94 to 102 of SEQ ID NO: 3. The CDR sequences within the heavy chain of 3F18 may be identified at amino acids 31 to 35, 50 to 65 and 98 to 107 of SEQ ID NO: 6. An antibody of the invention may comprise any one or more of the CDR sequences shown in FIG. 3. For example, an antibody of the invention may comprise one, two or all three of the amino acid sequences shown at residues 24 to 39, 55 to 61 and 94 to 102 of SEQ ID NO: 3. An antibody of the invention may alternatively or additionally comprise one, two or all three of the amino acid sequences shown at residues 31 to 35, 50 to 65 and 98 to 107 of SEQ ID NO: 6. An antibody of the invention may comprise all six amino acid sequences shown at residues 24 to 39, 55 to 61 and 94 to 102 of SEQ ID NO: 3 and 31 to 35, 50 to 65 and 98 to 107 of SEQ ID NO: 6.

An antibody of the invention may alternatively be or may comprise a variant of one of these specific sequences such a variant of the 3F18 antibody. For example, a variant may be a substitution, deletion or addition variant of any of the above amino acid sequences.

A variant antibody may comprise 1, 2, 3, 4, 5, up to 10, up to 20, up to 30 or more amino acid substitutions and/or deletions from the specific sequences and fragments discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| Ala | aliphatic, hydrophobic, neutral |
|---|---|
| Cys | polar, hydrophobic, neutral |
| Asp | polar, hydrophilic, charged (−) |
| Glu | polar, hydrophilic, charged (−) |
| Phe | aromatic, hydrophobic, neutral |
| Gly | aliphatic, neutral |
| His | aromatic, polar, hydrophilic, charged (+) |
| Ile | aliphatic, hydrophobic, neutral |
| Lys | polar, hydrophilic, charged(+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

Preferred "derivatives" or "variants" include those in which instead of the naturally occurring amino acid the amino acid which appears in the sequence is a structural analog thereof. Amino acids used in the sequences may also be derivatized or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Preferably variant antibodies according to the invention have an amino acid sequence which has more than 60%, or more than 70%, e.g. 75 or 80%, preferably more than 85%, e.g. more than 90 or 95% amino acid identity to SEQ ID Nos 3 or 6, or a fragment thereof. This level of amino acid identity may be seen across the full length of the relevant SEQ ID NO sequence or over a part of the sequence, such as across 20, 30, 50, 75, 100, 150, 200 or more amino acids, depending on the size of the full length polypeptide.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

The present invention thus provides antibodies having specific VH and VL amino acid sequences and variants and fragments thereof which maintain the function or activity of these VH and VL domains.

Accordingly, an antibody of the invention may comprise:

(a) a light chain variable region amino acid sequence of SEQ ID NO: 3;

(b) a fragment of at least 7 amino acids of (a) which retains the ability to specifically bind to TFPI; or (c) a variant of (a) having at least 70% amino acid sequence identity to a sequence of (a) and retaining the ability to specifically bind to TFPI.

An antibody of the invention may comprise:

(a) a heavy chain variable region amino acid sequence of SEQ ID NO: 6;

(b) a fragment of at least 7 amino acids of (a) which retains the ability to specifically bind to TFPI; or (c) a variant of (a) having at least 70% amino acid sequence identity to a sequence of (a) and retaining the ability to specifically bind to TFPI.

An antibody of the invention may comprise the light chain variable region of SEQ ID NO: 3 and the heavy chain variable region of SEQ ID NO: 6.

An antibody of the invention may comprise (a) the light chain variable region of SEQ ID NO: 3 and the heavy chain variable region of SEQ ID NO: 6;

(b) a variant of (a) in which one or both of the heavy chain and light chain sequences is modified such that it comprises a fragment of at least 7 amino acids of the sequence specified in (a); or (c) a variant of any of (a) or (b) in which one or both of the heavy and light chain sequences is modified such that it has at least 70% amino acid sequence identity to a sequence of (a) or (b)

wherein the antibody retains the ability to specifically bind to TFPI. The antibody may also retain one or more additional functions or activities of an antibody of the invention as described herein such as the ability to inhibit TFPI or the ability to shorten clotting time, optionally without leading to a drop in platelet numbers.

Preferred fragments and variants of SEQ ID NO: 3 will comprise (i) amino acids 24 to 39 of SEQ ID NO: 3; and/or (ii) amino acids 55 to 61 of SEQ ID NO: 3; and/or (iii) amino acids 94 to 102 of SEQ ID NO: 3. Preferred fragments and variants of SEQ ID NO: 6 will comprise (i) amino acids 31 to 35 of SEQ ID NO: 6; and/or (ii) amino acids 50 to 65 of SEQ ID NO: 6; and/or (iii) amino acids 98 to 107 of SEQ ID NO: 6.

As explained above, an antibody of the invention may bind to the same epitope or region as another antibody of the invention. Thus it will be seen that such an antibody may bind to the same epitope or region of TFPI as any of the specific antibodies, fragments and variants described herein.

The invention also relates to polynucleotides that encode antibodies of the invention. Thus, a polynucleotide of the invention may encode any antibody as described herein. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

In one embodiment, a polynucleotide of the invention comprises a sequence which encodes a VH or VL amino acid sequence as described above. For example, a polynucleotide of the invention may encode a polypeptide comprising the sequence of SEQ ID No: 3 or 6 or a variant or fragment thereof as described above. Such a polynucleotide may consist of or comprise a nucleic acid sequence of any one of SEQ ID NOs: 2, 4, 5 and 7. A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of SEQ ID NOs: 2, 4, 5 and 7. preferably at least 80 or 90% and more preferably at least 95%, 97% or 99% homologous thereto. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al (1984) Nucleic Acids Research 12, p 387-395).

The PILEUP and BLAST algorithms can also be used to calculate homology or line up sequences (typically on their default settings), for example as described in Altschul S. F. (1993) J Mol Evol 36:290-300; Altschul, S, F et al (1990) J Mol Biol 215:403-10.

Software for performing BLAST analysis is publicly available through the National Centre for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89:10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

Polynucleotide "fragments" according to the invention may be made by truncation, e.g. by removal of one or more nucleotides from one or both ends of a polynucleotide. Up to 10, up to 20, up to 30, up to 40, up to 50, up to 75, up to 100, up to 200 or more amino acids may be removed from the 3' and/or 5' end of the polynucleotide in this way. Fragments may also be generated by one or more internal deletions. Such fragments may be derived from a sequence of SEQ ID NOs: 2, 4, 5 or 7 or may be derived from a variant polynucleotide as described herein. Preferably such fragments are between 30 and 300 residues in length, e.g. 30 to 300, 30 to 200, 30 to 100, 100 to 200 or 200 to 300 residues. Alternatively, fragments of the invention may be longer sequences, for example comprising at least 50%, at least 60%, at least 70%, at least 80% or at least 90% of a full length polynucleotide of the invention.

An antibody of the invention may thus be produced from or delivered in the form of a polynucleotide which encodes, and is capable of expressing, it. Where the antibody comprises two or more chains, a polynucleotide of the invention may encode one or more antibody chains. For example, a polynucleotide of the invention may encode an antibody light chain, an antibody heavy chain or both. Two polynucleotides may be provided, one of which encodes an antibody light chain and the other of which encodes the corresponding antibody heavy chain. Such a polynucleotide or pair of polynucleotides may be expressed together such that an antibody of the invention is generated.

Polynucleotides of the invention can be synthesised according to methods well known in the art, as described by way of example in Sambrook et al (1989, Molecular Cloning—a laboratory manual; Cold Spring Harbor Press).

The nucleic acid molecules of the present invention may be provided in the form of an expression cassette which includes control sequences operably linked to the inserted sequence, thus allowing for expression of the antibody of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express an antibody of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for an antibody of the invention include mammalian HEK293T, CHO, HeLa and COS cells. Preferably the cell line selected will be one which is not only stable, but also allows for mature glycosylation and cell surface expression of a polypeptide.

Such cell lines of the invention may be cultured using routine methods to produce an antibody of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

In another aspect, the present invention provides compositions and formulations comprising molecules of the invention, such as the antibodies, polynucleotides, vectors and cells described herein. For example, the invention provides a pharmaceutical composition comprising one or more molecules of the invention, such as one or more antibodies of the invention, formulated together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g. intravenous, intramuscular or subcutaneous administration (e.g., by injection or infusion). Depending on the route of administration, the antibody may be coated in a material to protect the antibody from the action of acids and other natural conditions that may inactivate or denature the antibody.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In many cases, it will be preferable to include isotonic agents, for example, sugars, polyalcohols such as mannitol, sorbitol, or sodium chloride in the composition.

A pharmaceutical composition of the invention also may include a pharmaceutically acceptable anti-oxidant. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Therapeutic compositions typically must be sterile and stable under the conditions of manufacture and storage. The composition can be formulated as a solution, microemulsion, liposome, or other ordered structure suitable to high drug concentration.

Sterile injectable solutions can be prepared by incorporating the active agent (e.g. antibody) in the required amount in an appropriate solvent with one or a combination of ingredients enumerated above, as required, followed by sterilization microfiltration. Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Pharmaceutical compositions of the invention may comprise additional active ingredients as well as an antibody of the invention. As mentioned above, compositions of the invention may comprise one or more antibodies of the invention. They may also comprise additional therapeutic or prophylactic agents. For example, where a pharmaceutical composition of the invention is intended for use in the treatment of a bleeding disorder, it may additionally comprise one or more agents intended to reduce the symptoms of the bleeding disorder. For example, the composition may comprise one or more clotting factors. The composition may comprise one or more other components intended to improve the condition of the patient. For example, where the composition is intended for use in the treatment of patients suffering from unwanted bleeding such as patients undergoing surgery or patients suffering from trauma, the composition may comprise one or more analgesic, anaesthetic, immunosuppressant or anti-inflammatory agents.

Also within the scope of the present invention are kits comprising antibodies or other compositions of the invention and instructions for use. The kit may further contain one or more additional reagents, such as an additional therapeutic or prophylactic agent as discussed above.

The antibodies, other molecules and compositions of the present invention have numerous in vitro and in vivo therapeutic utilities involving the treatment and prevention of clotting related disorders. For example, these antibodies and compositions can be administered to cells in culture, in vitro or ex vivo, or to human subjects, e.g., in vivo, to prevent or treat a variety of disorders.

In particular, the present invention provides methods for the treatment of bleeding disorders or for the enhancement of blood clotting comprising administering to a patient in need thereof an effective amount of an antibody or other molecule or composition of the invention. For example, such methods may be for the treatment of clotting factor deficiencies such as haemophilia A, haemophilia B, Factor XI deficiency, Factor VII deficiency, thrombocytopenia or von Willebrand's disease. Such methods may be for the treatment of conditions accompanied by the presence of a clotting factor inhibitor. Such methods may be for the treatment of excessive bleeding. The antibodies and compositions of the invention may be used to treat patients before, during, or after surgery or anticoagulant therapy or after trauma. The antibodies and compositions described herein may be used in any such treatment or may be used in the manufacture of a medicament for use in any such treatment.

The antibodies and compositions of the present invention may be administered for prophylactic/preventitive and/or therapeutic treatments.

In therapeutic applications, antibodies or compositions are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". For example, where the treatment is for unwanted bleeding, therapy may be defined as a decrease in the amount of bleeding or suitable coagulation to stop the bleeding altogether.

In prophylactic or preventitive applications, antibodies or compositions are administered to a subject at risk of a disorder or condition as described above, in an amount sufficient to prevent or reduce the subsequent effects of the condition or one or more of its symptoms. An amount adequate to accomplish this is defined as a "prophylactically effective amount". For example, where the treatment is to prevent unwanted bleeding, a prophylactic effect may be defined as the prevention of bleeding or a reduced period or quantity of bleeding compared to that that would be seen in the absence of the modulator.

Effective amounts for each purpose will depend on the severity of the disease or injury as well as the weight and general state of the subject.

As used herein, the term "subject" includes any human or non-human animal. The term "non-human animal" includes all vertebrates, e.g., mammals and non-mammals, such as non-human primates, sheep, dogs, cats, horses, cows, chickens, amphibians, reptiles, etc.

An antibody or composition of the present invention may be administered via one or more routes of administration using one or more of a variety of methods known in the art. As will be appreciated by the skilled artisan, the route and/or mode of administration will vary depending upon the desired results. Preferred routes of administration for antibodies or compositions of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection. Alternatively, an antibody or composition of the invention can be administered via a non-parenteral route, such as a topical, epidermal or mucosal route of administration.

A suitable dosage of an antibody of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular antibody employed, the route of administration, the time of administration, the rate of excretion of the antibody, the duration of the treatment, other drugs, compounds and/or materials used in combination with the particular compositions employed, the age, sex, weight, condition, general health and prior medical history of the patient being treated, and like factors well known in the medical arts.

A suitable dose of an antibody of the invention may be, for example, in the range of from about 0.1 µg/kg to about 100 mg/kg body weight of the patient to be treated. For example, a suitable dosage may be from about 1 µg/kg to about 10 mg/kg body weight per day or from about 10 g/kg to about 5 mg/kg body weight per day.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Antibodies may be administered in a single dose or in multiple doses. The multiple doses may be administered via the same or different routes and to the same or different locations. Alternatively, antibodies can be administered as a sustained release formulation, in which case less frequent administration is required. Dosage and frequency may vary depending on the half-life of the antibody in the patient and the duration of treatment that is desired. The dosage and frequency of administration can also vary depending on whether the treatment is prophylactic or therapeutic. In prophylactic applications, a relatively low dosage may be administered at relatively infrequent intervals over a long period of time. In therapeutic applications, a relatively high dosage may be administered, for example until the patient shows partial or complete amelioration of symptoms of disease.

As mentioned above, antibodies of the invention may be co-administered with one or other more other therapeutic agents. The other agent may be an agent that will enhance the effects of the modulator. The other agent may be an agent that acts to enhance blood coagulation, such as a blood coagulation factor. In particular, the modulators of the invention may be co-administered with Factor VII or Factor VIIa. The other agent may be intended to treat other symptoms or conditions of the patient. For example, the other agent may be an analgesic, anaesthetic, immunosuppressant or anti-inflammatory agent.

Combined administration of two or more agents may be achieved in a number of different ways. In one embodiment, the antibody and the other agent may be administered together in a single composition. In another embodiment, the antibody and the other agent may be administered in separate compositions as part of a combined therapy. For example, the modulator may be administered before, after or concurrently with the other agent.

The present invention is further illustrated by the following examples which should not be construed as further limiting. The contents of all figures and all references, patents and published patent applications cited throughout this application are expressly incorporated herein by reference.

EXAMPLES

Example 1

Production and Characterisation of a Monoclonal Antibody Directed Against TFPI

Summary

Monoclonal antibodies were generated against tissue factor pathway inhibitor (TFPI). A monoclonal antibody having the desired binding specificity was identified, cloned and sequenced. This antibody was found to significantly reduce cuticle bleeding time in vivo, but to lead to no significant drop in platelet number.

Methods and Results

All kits were used according to the manufacturers' instructions. Abbreviations: HC: heavy chain; LC: light chain; VH: variable domain—heavy chain; VL: variable domain—light chain; PCR: polymerase chain reaction.

Immunisation and Fusion

Mice were immunized with both full length TFPI and the short version TFPIB161B which contains only the first two Kunitz domains. RBF mice were used for immunizations and production of mouse monoclonal antibodies. Injections were made subcutaneously in the back of the mice. 20 µg protein was mixed with complete Freund's adjuvant for the first injection. In the subsequent immunizations, incomplete Freund's adjuvant was used with same concentration of the antigen. Ten days after the last immunization, eye-blood from mice was screened by ELISA for TFPI specific antibodies. Mice with positive serum titres were boosted with 10 µg of TFPI by intravenous injection, and sacrificed after three days. The spleens were removed aseptically and dispersed to a single cell suspension. Fusion of spleen cells and myeloma cells was done by the PEG-method or by electrofusion.

Binding Assay: ELISA

Immunoplates were coated with anti-mouse IgG. Culture supernatants from the hybridoma cells were added to the plates and, after washing, soluble biotinylated human TFPI or TFPIB161B was added to test for specific binding.

Neutralizing Assays: FXa Assay and TF/FVIIa/FXa Assay

FXa inhibition assay: a fixed concentration of TFPI giving rise to 90% inhibition of FXa was pre-incubated with culture supernatants from hybridoma cells containing anti TFPI monoclonal antibodies and added to FXa plus FXa-specific chromogenic substrate. This assay addresses TFPI binding to FXa (the K2 domain)

FVIIa/TF/FXa inhibition assay: 1) Incubation of culture supernatants from hybridoma cells containing anti TFPI monoclonal antibodies anti and fixed TFPI (90% inhibition of FVIIa/TF); 2) Incubation of TFPI+FVIIa+TF+FXa; 3) Addition of FX (FX>>FXa) followed by incubation with FXa chromogenic substrate.

Dilute Prothrombin Time (dPT)

A dilute Prothrombin (PT) analysis: human plasma in combination with diluted human thromboplastin (TF source). Clot time in the plasma was measured upon addition of increasing protein A purified TFPI monoclonal antibody concentrations to look for dose dependent reduction of clotting time. FVIIa (25 nM) was the positive control and must shorten this clot time.

Binding Interaction Analysis

Binding interaction analysis was obtained by Surface Plasmon Resonance in a Biacore 3000. Capture of the relevant monoclonal antibody at a fixed concentration was obtained with immobilised mouse anti-IgG. Different concentrations of TFPI were tested. Determination of binding constants ($k_{on}$, $k_{off}$, $K_D$) was obtained assuming a 1:1 interaction of TFPI and the antibody of interest.

Thrombelastography

Records the kinetic of clot formation and fibrinolysis in whole blood. Haemophilia A like condition is induced by pre-incubating the blood with neutralizing anti-FVIII IgG.

In Vivo Studies

Rabbits were made transient haemophilic by iv. administration of 2000 RBU/kg of monoclonal anti-FVIII-antibodies. After 10 minutes, the rabbits received 12000 U/kg of anti-TFPI-antibody (3F18; 1.93 mg/kg). Cuticle bleeding was induced 45 minutes after anti-FVIII-antibody administration.

The 3F18 antibody caused a significant reduction in cuticle bleeding time, comparable with the effect of 10 mg/kg rFVIIa (FIG. 1). Administration of the 3F18 antibody led to no significant drop in platelet number (FIG. 5).

Antibody Cloning and Sequencing

Murine heavy chain and light chain sequence for anti-TFPI antibodies were cloned from a hybridoma: TFPI-3F18A4B1 (abbreviated herein to 3F18). Total RNA, extracted from hybridoma cells using the RNeasy-Mini Kit from Qiagen, was used as templates for cDNA synthesis. cDNA was synthesized in a 5'-RACE reaction using the SMART™ RACE cDNA amplification kit from Clontech. Subsequent target amplification of HC and LC sequences was performed by PCR using Phusion Hot Star polymerase (Finnzymes) and the universal primer mix (UPM) included in the SMART™ RACE kit as a forward primer. A reverse primer with the following sequence was used for HC (VH domain) amplification: 5'-CCCTTGACCAGGCATCCCAG-3' (primer #129) (SEQ ID NO: 8). A reverse primer with the following sequence was used for LC amplification: 5'-GCTCTAGACTAACACTCATTCCTGTTGAAGCTCTTG-3' (primer #69) (SEQ ID NO: 9).

PCR products were separated by gel electrophoresis, extracted using the GFX PCR DNA and Gel Band Purification Kit from GE Healthcare Bio-Sciences and cloned for sequencing using a Zero Blunt TOPO PCR Cloning Kit and chemically competent TOP10 *E. coli* from Invitrogen. Colony PCR was performed on selected colonies using an AmpliTaq Gold Mas-ter Mix from Applied Biosystems and M13uni/M13rev primers. Colony PCR clean-up was performed using the ExoSAP-IT enzyme mix (usb). Sequencing was performed at MWG Biotech, Martinsried Germany using either M13uni(−21)/M13rev(−29) or T3/T7 sequencing primers. Sequences were analyzed and annotated using the Vector NTI program.

From the hybridoma TFPI-3F18A4B1 a single unique murine kappa type LC was identified and a single unique murine HC, subclass IgG1. VH & VL Sequences are shown in FIG. 2, leader peptide sequences are not included.

The invention claimed is:

1. An isolated antibody that specifically binds to tissue factor pathway inhibitor (TFPI) comprising
   amino acids 24 to 39 of SEQ ID NO: 3;
   amino acids 55 to 61 of SEQ ID NO: 3;
   amino acids 94 to 102 of SEQ ID NO: 3;
   amino acids 31 to 35 of SEQ ID NO: 6;
   amino acids 50 to 65 of SEQ ID NO: 6; and
   amino acids 98 to 107 of SEQ ID NO: 6.

2. The isolated antibody according to claim 1 comprising the light chain variable region of SEQ ID NO: 3 and the heavy chain variable region of SEQ ID NO: 6.

3. The isolated antibody according to claim 1 that reduces clotting time in vivo without significantly reducing platelet levels.

4. The isolated antibody according to claim 1 which is a monoclonal antibody.

5. The isolated antibody of claim 1, wherein the antibody reduces clotting time in human FVIII-deficient plasma.

6. The isolated antibody of claim 1, wherein the antibody reduces clotting time in human FVIII-deficient whole blood.

7. A pharmaceutical composition comprising an isolated antibody according to claim 1 and a pharmaceutically acceptable carrier or diluent.

8. A method of treating a bleeding disorder in a subject or for stimulating blood clotting in a subject, the method comprising administering to said subject the isolated antibody according to claim 1 for treatment of a bleeding disorder or the stimulation of blood clotting.

* * * * *

SEQUENCE LISTING

```
<160> NUMBER OF SEQ ID NOS: 9

<210> SEQ ID NO 1
<211> LENGTH: 276
<212> TYPE: PRT
<213> ORGANISM: Homo sapiens
<220> FEATURE:
<221> NAME/KEY: DOMAIN
<222> LOCATION: (26)..(76)
<223> OTHER INFORMATION: Kunitz domain 1
<220> FEATURE:
<221> NAME/KEY: DOMAIN
<222> LOCATION: (97)..(147)
<223> OTHER INFORMATION: Kunitz domain 2
<220> FEATURE:
<221> NAME/KEY: DOMAIN
<222> LOCATION: (188)..(238)
<223> OTHER INFORMATION: Kunitz domain 3

<400> SEQUENCE: 1

Asp Ser Glu Glu Asp Glu Glu His Thr Ile Ile Thr Asp Thr Glu Leu
1               5                   10                  15

Pro Pro Leu Lys Leu Met His Ser Phe Cys Ala Phe Lys Ala Asp Asp
                20                  25                  30

Gly Pro Cys Lys Ala Ile Met Lys Arg Phe Phe Phe Asn Ile Phe Thr
            35                  40                  45

Arg Gln Cys Glu Glu Phe Ile Tyr Gly Gly Cys Glu Gly Asn Gln Asn
        50                  55                  60

Arg Phe Glu Ser Leu Glu Glu Cys Lys Lys Met Cys Thr Arg Asp Asn
65                  70                  75                  80

Ala Asn Arg Ile Ile Lys Thr Thr Leu Gln Gln Glu Lys Pro Asp Phe
```

-continued

```
                        85                  90                  95
Cys Phe Leu Glu Glu Asp Pro Gly Ile Cys Arg Gly Tyr Ile Thr Arg
                100                 105                 110

Tyr Phe Tyr Asn Asn Gln Thr Lys Gln Cys Glu Arg Phe Lys Tyr Gly
            115                 120                 125

Gly Cys Leu Gly Asn Met Asn Asn Phe Glu Thr Leu Glu Glu Cys Lys
        130                 135                 140

Asn Ile Cys Glu Asp Gly Pro Asn Gly Phe Gln Val Asp Asn Tyr Gly
145                 150                 155                 160

Thr Gln Leu Asn Ala Val Asn Asn Ser Leu Thr Pro Gln Ser Thr Lys
                165                 170                 175

Val Pro Ser Leu Phe Glu Phe His Gly Pro Ser Trp Cys Leu Thr Pro
            180                 185                 190

Ala Asp Arg Gly Leu Cys Arg Ala Asn Glu Asn Arg Phe Tyr Tyr Asn
        195                 200                 205

Ser Val Ile Gly Lys Cys Arg Pro Phe Lys Tyr Ser Gly Cys Gly Gly
    210                 215                 220

Asn Glu Asn Asn Phe Thr Ser Lys Gln Glu Cys Leu Arg Ala Cys Lys
225                 230                 235                 240

Lys Gly Phe Ile Gln Arg Ile Ser Lys Gly Leu Ile Lys Thr Lys
                245                 250                 255

Arg Lys Arg Lys Lys Gln Arg Val Lys Ile Ala Tyr Glu Glu Ile Phe
            260                 265                 270

Val Lys Asn Met
        275

<210> SEQ ID NO 2
<211> LENGTH: 339
<212> TYPE: DNA
<213> ORGANISM: Mus musculus
<220> FEATURE:
<221> NAME/KEY: CDS
<222> LOCATION: (1)..(339)

<400> SEQUENCE: 2 gat gtt gtg atg acc cag act cca ctc act ttg tcg gtt acc att gga        48
Asp Val Val Met Thr Gln Thr Pro Leu Thr Leu Ser Val Thr Ile Gly
1               5                   10                  15 caa cca gct tcc atc tct tgc aag tca agt cag agc ctc tta gat agt        96
Gln Pro Ala Ser Ile Ser Cys Lys Ser Ser Gln Ser Leu Leu Asp Ser
            20                  25                  30 gat gga aaa acc tat tta aat tgg tta tta cag agg cca ggc gag tct       144
Asp Gly Lys Thr Tyr Leu Asn Trp Leu Leu Gln Arg Pro Gly Glu Ser
        35                  40                  45 cca aag ctc ctt atc tat ctg gtg tct aaa ctg gac tct gga gtc cct       192
Pro Lys Leu Leu Ile Tyr Leu Val Ser Lys Leu Asp Ser Gly Val Pro
    50                  55                  60 gac agg ttc act ggc agt gga tca ggg aca gat ttc aca ctg aaa atc       240
Asp Arg Phe Thr Gly Ser Gly Ser Gly Thr Asp Phe Thr Leu Lys Ile
65                  70                  75                  80 agc aga gtg gag gct gag gat ttg gga gtt tat tac tgc tta caa ggt       288
Ser Arg Val Glu Ala Glu Asp Leu Gly Val Tyr Tyr Cys Leu Gln Gly
                85                  90                  95 aca cat ttt cct cac acg ttc gga ggg ggg acc aag ctg gaa ata aaa       336
Thr His Phe Pro His Thr Phe Gly Gly Gly Thr Lys Leu Glu Ile Lys
            100                 105                 110 cgg                                                                    339
Arg
```

<210> SEQ ID NO 3
<211> LENGTH: 113
<212> TYPE: PRT
<213> ORGANISM: Mus musculus
<220> FEATURE:
<221> NAME/KEY: DOMAIN
<222> LOCATION: (24)..(39)
<223> OTHER INFORMATION: CDR
<220> FEATURE:
<221> NAME/KEY: DOMAIN
<222> LOCATION: (55)..(61)
<223> OTHER INFORMATION: CDR
<220> FEATURE:
<221> NAME/KEY: DOMAIN
<222> LOCATION: (94)..(102)
<223> OTHER INFORMATION: CDR

<400> SEQUENCE: 3

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Glu Ser
        35                  40                  45

Pro Lys Leu Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Leu Gln Gly
                85                  90                  95

Thr His Phe Pro His Thr Phe Gly Gly Gly Thr Lys Leu Glu Ile Lys
            100                 105                 110

Arg

<210> SEQ ID NO 4
<211> LENGTH: 339
<212> TYPE: DNA
<213> ORGANISM: Mus musculus

<400> SEQUENCE: 4
ccgttttatt tccagcttgg tccccctcc gaacgtgtga ggaaaatgtg taccttgtaa      60
gcagtaataa actcccaaat cctcagcctc cactctgctg attttcagtg tgaaatctgt    120
ccctgatcca ctgccagtga acctgtcagg gactccagag tccagtttag acaccagata   180
gataaggagc tttggagact cgcctggcct ctgtaataac caatttaaat aggttttttcc  240 atcactatct aagaggctct gacttgactt gcaagagatg gaagctggtt gtccaatggt   300
aaccgacaaa gtgagtggag tctgggtcat cacaacatc                           339

<210> SEQ ID NO 5
<211> LENGTH: 354
<212> TYPE: DNA
<213> ORGANISM: Mus musculus
<220> FEATURE:
<221> NAME/KEY: CDS
<222> LOCATION: (1)..(354)

<400> SEQUENCE: 5 gaa gtg aag ctg gta gag tct ggg gga ggc ttg gtg aag cct gga ggg      48
Glu Val Lys Leu Val Glu Ser Gly Gly Gly Leu Val Lys Pro Gly Gly
1               5                   10                  15 tcc ctg aga ctc tcc tgt gca gcc tct gga ttc act ttc agt aac tat      96
Ser Leu Arg Leu Ser Cys Ala Ala Ser Gly Phe Thr Phe Ser Asn Tyr

```
                    20                  25                  30
gcc ctg tct tgg gtt cgc cag act cca gac aag agg ctg gag tgg gtc      144
Ala Leu Ser Trp Val Arg Gln Thr Pro Asp Lys Arg Leu Glu Trp Val
         35                  40                  45 gca tcc att agt agt ggt ggt gcc acc tac tat cca gac agt gtg gag      192
Ala Ser Ile Ser Ser Gly Gly Ala Thr Tyr Tyr Pro Asp Ser Val Glu
 50                  55                  60 ggc cga ttc acc atc tcc aga gat aat gtc agg aac atc ctg tac ctg      240
Gly Arg Phe Thr Ile Ser Arg Asp Asn Val Arg Asn Ile Leu Tyr Leu
 65                  70                  75                  80 caa atg agc agt ctg cag tct gag gac acg gcc atg tat tac tgt aca      288
Gln Met Ser Ser Leu Gln Ser Glu Asp Thr Ala Met Tyr Tyr Cys Thr
                 85                  90                  95 aga gga gcc tac ggc tcg gac tac ttt gac tac tgg ggc caa ggc acc      336
Arg Gly Ala Tyr Gly Ser Asp Tyr Phe Asp Tyr Trp Gly Gln Gly Thr
            100                 105                 110 act ctc aca gtc tcc tca                                               354
Thr Leu Thr Val Ser Ser
        115

<210> SEQ ID NO 6
<211> LENGTH: 118
<212> TYPE: PRT
<213> ORGANISM: Mus musculus
<220> FEATURE:
<221> NAME/KEY: DOMAIN
<222> LOCATION: (31)..(35)
<223> OTHER INFORMATION: CDR
<220> FEATURE:
<221> NAME/KEY: DOMAIN
<222> LOCATION: (50)..(65)
<223> OTHER INFORMATION: CDR
<220> FEATURE:
<221> NAME/KEY: DOMAIN
<222> LOCATION: (98)..(107)
<223> OTHER INFORMATION: CDR

<400> SEQUENCE: 6

Glu Val Lys Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Tyr
             20                  25                  30

Ala Leu Ser Trp Val Arg Gln Thr Pro Asp Lys Arg Leu Glu Trp Val
         35                  40                  45

Ala Ser Ile Ser Ser Gly Gly Ala Thr Tyr Tyr Pro Asp Ser Val Glu
 50                  55                  60

Gly Arg Phe Thr Ile Ser Arg Asp Asn Val Arg Asn Ile Leu Tyr Leu
 65                  70                  75                  80

Gln Met Ser Ser Leu Gln Ser Glu Asp Thr Ala Met Tyr Tyr Cys Thr
                 85                  90                  95

Arg Gly Ala Tyr Gly Ser Asp Tyr Phe Asp Tyr Trp Gly Gln Gly Thr
            100                 105                 110

Thr Leu Thr Val Ser Ser
        115

<210> SEQ ID NO 7
<211> LENGTH: 354
<212> TYPE: DNA
<213> ORGANISM: Mus musculus

<400> SEQUENCE: 7
tgaggagact gtgagagtgg tgccttggcc ccagtagtca aagtagtccg agccgtaggc    60
```

-continued

```
tcctcttgta cagtaataca tggccgtgtc ctcagactgc agactgctca tttgcaggta    120
caggatgttc ctgacattat ctctggagat ggtgaatcgg ccctccacac tgtctggata    180
gtaggtggca ccaccactac taatggatgc gacccactcc agcctcttgt ctggagtctg    240
gcgaacccaa gacagggcat agttactgaa agtgaatcca gaggctgcac aggagagtct    300
cagggaccct ccaggcttca ccaagcctcc cccagactct accagcttca cttc          354
```

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8

```
cccttgacca ggcatcccag                                                 20
```

<210> SEQ ID NO 9
<211> LENGTH: 36
<212> TYPE: DNA
<213> ORGANISM: Artificial
<220> FEATURE:
<223> OTHER INFORMATION: primer

<400> SEQUENCE: 9

```
gctctagact aacactcatt cctgttgaag ctcttg                               36
```